United States Patent [19]

Foy

[11] Patent Number: 5,170,797
[45] Date of Patent: Dec. 15, 1992

[54] THERMODILUTION INJECTATE SYSTEM WITH FILTER

[75] Inventor: Glenn E. Foy, Camarillo, Calif.

[73] Assignee: BOC Health Care, Inc., New Providence, N.J.

[21] Appl. No.: 724,045

[22] Filed: Jul. 1, 1991

[51] Int. Cl.⁵ .............................................. A61B 5/02
[52] U.S. Cl. .................... 128/713; 604/53; 604/113; 604/66
[58] Field of Search ............... 128/713, 692, 400, 399; 604/218, 113, 248, 65, 66, 52, 53

[56]  References Cited

U.S. PATENT DOCUMENTS

| | | | |
|---|---|---|---|
| 4,502,488 | 3/1985 | Degironimo et al. | 128/713 |
| 4,508,123 | 4/1985 | Wyatt et al. | 128/713 |
| 4,713,060 | 12/1987 | Riuli | 604/218 |
| 4,819,655 | 4/1989 | Webler | 128/713 |
| 4,941,475 | 7/1990 | Williams et al. | 128/713 |

OTHER PUBLICATIONS

Clyde-Disposable Filter Device.

Primary Examiner—Francis Jaworski
Assistant Examiner—George Manuel
Attorney, Agent, or Firm—Roger M. Rathbun; Larry R. Cassett

[57] ABSTRACT

A filter having a microporous hydrophilic membrane is utilized in a thermodilution set up wherein the filter is positioned downstream from the injectate reservoir, the syringe and most of the fittings through which bacteria or other harmful materials could enter the bolus of injectate. The filter thus traps bacteria and particulates and prevents the material that may have inadvertently entered the injectate stream from being introduced into the patient. The filter is relatively inexpensive and is commerically available having a pore size of about 0.2 um while allowing typical thermodilution injectate flows of about 150 cc/min.

8 Claims, 1 Drawing Sheet

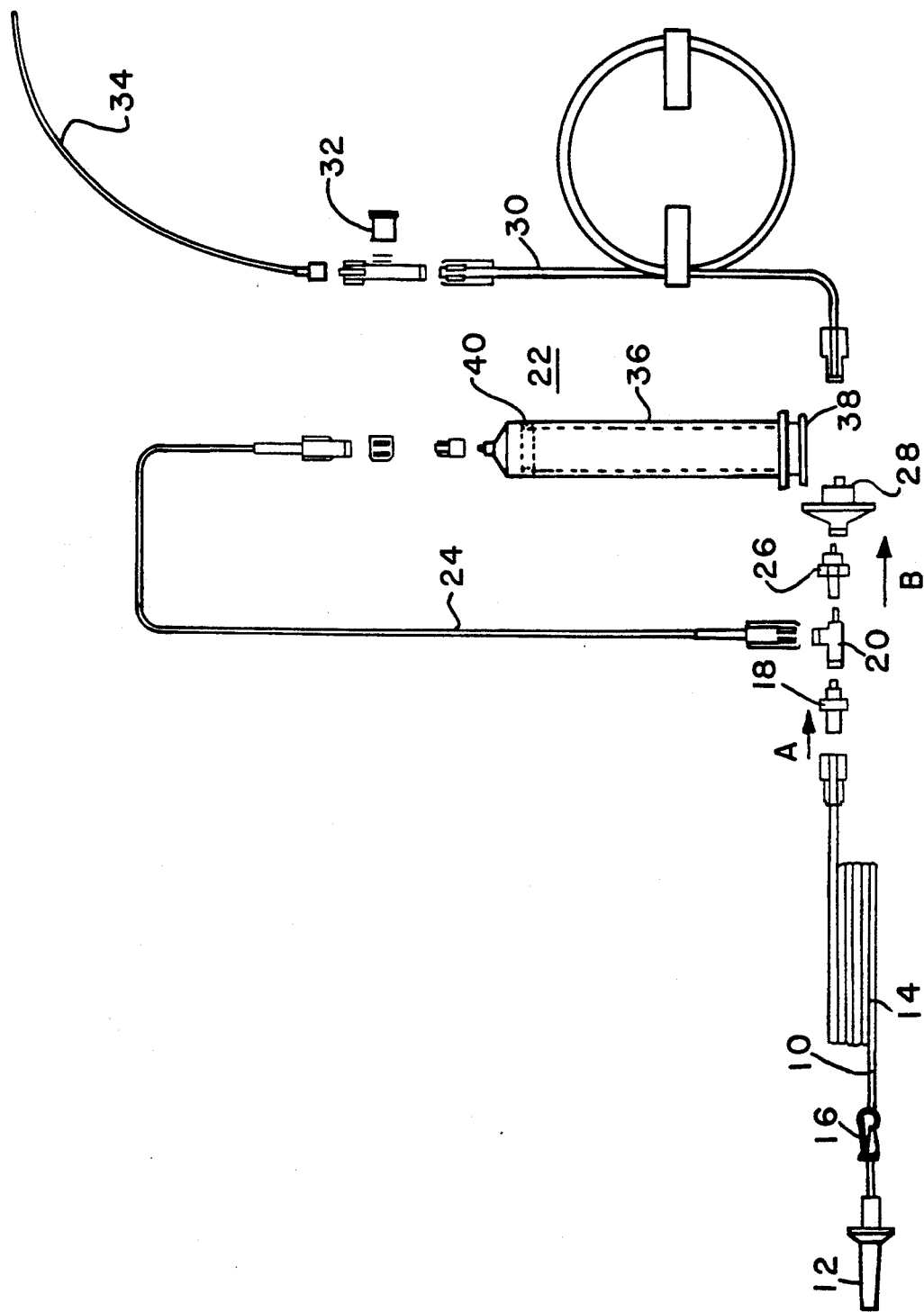

THERMODILUTION INJECTATE SYSTEM WITH FILTER

BACKGROUND OF THE INVENTION

This invention relates to a system for injecting a bolus of liquid into a patient to carry out a measurement of cardiac output by thermodilution and, more particularly, to a system including a filter to prevent the introduction of bacteria or particulates along with the injectate into the patient.

One of the common procedures during operations is the monitoring of cardiac output. Although some systems have been proposed to carry out noninvasive cardiac output, by far the most common method is to utilize thermodilution. The method is invasive and utilizes a catheter, such as a Swan Ganz catheter, that is positioned within the heart. A liquid having a known temperature, normally chilled, is introduced through the catheter into the right atrium and a temperature sensor, positioned in the pulmonary artery senses the change in temperature of the blood exiting the heart. By a correlation of time and temperature drop, a measurement of cardiac output can be readily calculated.

In common practice, the injection of the cold bolus of liquid is carried out manually by attending personnel through use of a syringe that has been chilled to the appropriate temperature and, in recent times, the injection may be automatically carried out by a pump means of certain types.

In either case, whether the injection of liquid is achieved by a manually operated syringe, or by an automated pump, a problem exists in insuring that the injectate itself does not introduce bacteria or other harmful substances into the patient. This is particularly important in that the injectate itself is introduced directly into the heart and therefore is carried rapidly through the patient's circulatory system.

In typical thermodilution applications, multiple injections are carried out on the patient over a fairly extended period of time. Generally, the same set up may be used, for example, for 72 hours and each reading of cardiac output may require 3-5 injections to insure the integrity of the cardiac output results.

Accordingly, there is an opportunity for bacteria or other contaminants to enter the system and thrive in the moist environment and eventually find its way into the injectate liquid that is delivered to the patient. One means could be through the various connectors in the tubing, stopcocks, leakage from the continuous use or the phenonema known as blow by. In that phenomena, liquid injectate is forced past the normal syringe seal when high flows are used, typical of thermodilution in the range of 150-220 cc./min, and the seal between the syringe plunger and inside of the syringe barrel cannot take the momentary high pressure. Thus some liquid leaks past the seal outside the closed environment within the syringe. That liquid may remain on the outside of the seal within the syringe barrel and later be reintroduced past the seal and into the injectate or later uses of the syringe. Also, since the external part of the syringe plunger is outside the closed environment, it is touched by personnel and contamination can thus directly infect the plunger and migrate to the interior of the syringe.

Such blow by thus could allow bacteria to form in the liquid during the time outside the closed environment of the syringe and thus it is a possible source of contamination.

In addition, of course, the syringe and/or other components may become unsterile by openings in the sterile packaging during shipping, handling or the like.

A study of the problems of introduction of bacteria or other contaminants into the thermodilution injectate is reviewed in an article in Heart and Lung, March 1988, Vol. 17, No 2 pgs 121-128 entitled "Sterility and Efficiency of Two Methods of Cardiac Output Determination: Closed Loop and Capped Syringe Methods".

One solution currently proposed to lessen the risk of bacteria contamination is described in Riuli U.S. Pat. No. 4,713,060 where a sheath is provided enclosing the otherwise open portion of a syringe to prevent foreign contamination from entering the syringe. Again, however, the problem of blow by is not completely solved in that the liquid that leaks past the syringe seal may remain within the sheath and provide an environment for bacteria growth. That liquid can later be reintroduced back through the syringe seal and contaminate the injectate that is directed to the patient.

SUMMARY OF THE INVENTION

The present invention provides an improved thermodilution system that includes a filter that acts as a barrier to prevent bacteria and particulates from passing along with the injectate into the patient.

In particular, a microporous filter is utilized in the system downstream of the pump, syringe and most all of the possible sources of bacteria or other contamination. The filter is placed as close to the actual catheter that is positioned within the patient so that it traps the bacteria from entering the patient. The filter itself is of the type currently available for use with syringes that administer one time injections, such as for epideral anesthesia, cardiac block, spinal anesthesia and the like and comprises a microporous membrane having a 0.2 um pore size, yet it can allow relatively high flows, i.e. 150 cc/min without difficulties.

Since such typical filter membranes are also hydrophilic, there is an additional advantage that entrapped air in the injectate is also prevented by the filter from entering the patient where such air could cause harm.

One major advantage of the filter barrier is that it acts as a final screen of the injectate liquid and thus will filter out bacteria introduced via any upstream source, thus not only is the syringe eliminated as a possible source of such bacteria, but the connections, tubing, liquid reservoir and all other components can be downplayed as sources where the bacteria may inadvertently enter the injectate.

As a further advantage, the filter itself may be readily available commercially and one such filter is marked as the Super DIL Syringe Filter by Gelman Sources of Ann Arbor, Mich. That filter is generally sold for affixing on the end of a syringe for one shot or single use applications and is inexpensive.

Accordingly, by the use of such filter downstream of the areas where entering of bacteria is likely, the actual injectate that enters the patient can be filtered and bacteria removed to enhance the safety of the liquid injectate administered to the patient.

BRIEF DESCRIPTION OF THE DRAWINGS

The Figure is a schematic of a typical syringe type of thermodilution set up having a filter in accordance with the present invention.

DESCRIPTION OF THE PREFERRED EMBODIMENT

Taking the Figure, there is shown a schematic, in exploded form, of a typical thermodilution set up and having included therein the filter means of the present invention.

As shown, a conduit 10 has, at one end thereof, a connector 12 that is adapted to connect to a reservoir of fluid (not shown) such as saline solution. The conduit 10 is coiled, at 14, and such coil 14 is conventionally submerged on ice water in order to bring the temperature of the fluid injectate to approximately 1 degree Celsius. Alternatively, the fluid may be at room temperature. A valve 16 is provided in conduit 10 to control the supply of fluid as desired and conventionally, the reservoir is located at a predetermined height above the patient to insure the pressure of fluid is within certain limits.

At the other end of conduit 10, a check valve 18 is located and which allows the fluid through check valve 18 only in the direction of the arrow A. The downstream end of check valve 18 connects to a tee 20. A syringe 22 connects to the middle connection of tee 20 through tubing 24 and the remaining connection of tee 20 is connected to a further check valve 26 that allows fluid to pass therethrough only in the direction of the arrow B. A filter 28 is connected to the other end of check valve 26, the purpose of which will be later explained.

The remaining elements of the thermodilution set up are conventional and include tubing 30 that connects filter 26 to temperature sensor 32. A typical temperature sensor may be that described in Barker, U.S. Pat. No. 4,476,877.

A thermodilution catheter 34 is thereafter connected to temperature sensor 32 and which delivers the injectate fluid to the patient's heart to carry out the thermodilution process and to ultimately determine cardiac output.

Syringe 22 is also conventional and includes the syringe barrel 36 within which moves the piston 38. A seal 40 at the internal end of piston 38 forms a fluid seal against the internal surface of barrel 36 during operation of the syringe to both suck fluid into the syringe 22 and to pump fluid injectate out of syringe 22.

In operation of the thermodilution setup, the syringe 22 is operated to withdraw piston 38 from barrel 36 thereby drawing the liquid injectate from the reservoir, (now shown) through tubing 10 and check valve 18. The liquid injectate is cooled as it passes through coil 14 which is generally immersed in an ice bath. Thus, syringe 22 is filled with the desired quantity of liquid injectate, preferably about 10 cc. The cardiac computer is then activated and the syringe piston 8 is forced inwardly to pump the liquid injectate from the syringe 22 out through tube 24, the tee 20, check valve 26 filter 28 and finally through temperature sensor 32 into the thermodilution catheter 34 to be introduced into the patient. Readings are then taken by the computer to indicate cardiac output.

As can be seen, the microporous filter 28 is positioned downstream of the syringe 22 as well as downstream from most of the various fittings that could be sources for the entry of bacteria or other contaminants. Therefore, the bacteria that could enter the system through fittings, the reservoir, or due to operation of the syringe (including blow by) is caught before it progresses further toward and possibly into the thermodilution catheter. In addition, since the filter 28 contains a hydrophilic microporous membrane, air within the liquid injectate is not allowed to enter the patient as it is trapped by filter 28. With the pore size of 0.2 um, however, relatively high flows can be utilized while still trapping the bacteria and particulates.

It will be understood that the scope of this invention is not limited to the particulars specific embodiment disclosed herein, by way of example, but only by the scope of the appended claims, including this equivalence.

I claim:

1. A system for injecting a bolus of liquid at a known temperature into a patient through a catheter to carry out the measurement of cardiac output by means of thermodilution, comprising:
   a catheter, a reservoir for containing a supply of liquid injectate;
   conduit means for providing a path for said liquid injectate between said reservoir and the catheter;
   a pump means intermediate said reservoir and said catheter, said pump means communicating with said conduit means and adapted to force a predetermined quantity of liquid injectate from said reservoir into the catheter; and
   a filter means in said conduit means located immediately upstream of the catheter, said filter means adapted for removing bacteria and other particulate material from the liquid injectate prior to the liquid injectate entering the catheter.

2. A system as defined in claim 1 wherein said conduit means includes at least check valve means, fittings and stopcock means for preventing contamination from migrating into the liquid injectate.

3. A system as defined in claim 1 wherein said pump means is a manually operated syringe.

4. A system as defined in claim 1 wherein said pump means comprises an automatic pump.

5. A system as defined in claim 1 wherein said filter means includes a microporous membrane adapted for said liquid injectate to flow, said filter means having a pore size no larger than about 0.2 um.

6. A system as defined in claim 5 wherein said microporous membrane is hydrophilic.

7. A method of introducing a liquid injectate into a catheter delivery system the liquid injectate into a patient's heart to carry out the measurement of cardiac output by thermodilution, comprising the steps of;
   providing a supply of liquid injectate having a predetermined temperature;
   pumping a known quantity of the liquid injectate from the supply into the catheter and;
   bacterial filtering the liquid injectate immediately prior to the liquid injectate entering the catheter.

8. A method of introducing a liquid injectate into a patient's heart as defined in claim 7 wherein said pumping step comprises providing a syringe, and further comprises withdrawing the syringe plunger to receive liquid injectate into the syringe and forcing the plunger into the syringe to cause the liquid injectate to flow into the catheter.

* * * * *